(12) United States Patent
Champeaux et al.

(10) Patent No.: US 10,722,450 B2
(45) Date of Patent: *Jul. 28, 2020

(54) PROCESS FOR TREATING THE HAIR WITH AT LEAST ONE SILICONE FUNCTIONALIZED WITH AT LEAST ONE ALKOXYSILANE UNIT, AND STEAM

(71) Applicant: L'Oreal, Paris (FR)

(72) Inventors: Melissa Champeaux, Paris (FR); Gregory Plos, Paris (FR); Gabin Vic, Semoy (FR); Frederic Woodland, Gagny (FR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/547,166

(22) PCT Filed: Jan. 27, 2016

(86) PCT No.: PCT/EP2016/051712
§ 371 (c)(1),
(2) Date: Jul. 28, 2017

(87) PCT Pub. No.: WO2016/120334
PCT Pub. Date: Aug. 4, 2016

(65) Prior Publication Data
US 2018/0021246 A1    Jan. 25, 2018

(30) Foreign Application Priority Data
Jan. 29, 2015 (FR) ...................... 15 50706

(51) Int. Cl.
*A61K 8/898* (2006.01)
*A45D 7/06* (2006.01)
*A61Q 5/06* (2006.01)

(52) U.S. Cl.
CPC ............. *A61K 8/898* (2013.01); *A45D 7/06* (2013.01); *A61Q 5/06* (2013.01); *A61K 2800/87* (2013.01); *A61K 2800/884* (2013.01)

(58) Field of Classification Search
USPC ......................................................... 424/70
See application file for complete search history.

(56) References Cited

U.S. PATENT DOCUMENTS

| | | |
|---|---|---|
| 2,047,398 A | 7/1936 | Voss et al. |
| 2,102,113 A | 12/1937 | Djordjevitch |
| 2,723,248 A | 11/1955 | Wright |
| 3,579,629 A | 5/1971 | Pasero et al. |
| 3,589,978 A | 6/1971 | Kamal et al. |
| 3,716,633 A | 2/1973 | Viout et al. |
| 3,810,977 A | 5/1974 | Levine et al. |
| 3,836,537 A | 9/1974 | Boerwinkle et al. |
| 3,910,862 A | 10/1975 | Barabas et al. |
| 3,925,542 A | 12/1975 | Viout et al. |
| 3,946,749 A | 3/1976 | Papantoniou |
| 3,966,403 A | 6/1976 | Papantoniou et al. |
| 3,966,404 A | 6/1976 | Papantoniou et al. |
| 3,990,459 A | 11/1976 | Papantoniou |
| 4,031,307 A | 6/1977 | DeMartino et al. |
| 4,128,631 A | 12/1978 | Lundmark et al. |
| 4,129,711 A | 12/1978 | Viout et al. |
| 4,131,576 A | 12/1978 | Iovine et al. |
| 4,137,208 A | 1/1979 | Elliott |
| 4,165,367 A | 8/1979 | Chakrabarti |
| 4,166,473 A | 9/1979 | Bauer et al. |
| 4,223,009 A | 9/1980 | Chakrabarti |
| 4,282,203 A | 8/1981 | Jacquet et al. |
| 4,289,752 A | 9/1981 | Mahieu et al. |
| 4,341,229 A | 7/1982 | Bauer et al. |
| 4,957,732 A | 9/1990 | Grollier et al. |
| 5,520,199 A | 5/1996 | Sturla |
| 5,520,200 A | 5/1996 | Sturla |
| 5,679,324 A | 10/1997 | Lisboa et al. |
| 8,217,113 B2 | 7/2012 | Scheim et al. |
| 9,539,199 B2 | 1/2017 | Beer et al. |
| 2006/0110351 A1* | 5/2006 | Koehler ............... A61K 8/585 424/70.12 |
| 2007/0232729 A1 | 10/2007 | Briehn et al. |
| 2010/0258141 A1 | 10/2010 | Paul et al. |
| 2010/0307528 A1 | 12/2010 | Restle et al. |
| 2012/0064018 A1 | 3/2012 | Schultze et al. |
| 2013/0142750 A1 | 6/2013 | Fair et al. |

(Continued)

FOREIGN PATENT DOCUMENTS

| | | |
|---|---|---|
| DE | 2330956 A1 | 1/1974 |
| EP | 0080976 A1 | 6/1983 |

(Continued)

OTHER PUBLICATIONS

U.S. Appl. No. 15/547,142, filed Jul. 2017, Plos et al.*
International Search Report for PCT/EP2016/051697, dated Mar. 21, 2016.
International Search Report for PCT/EP2016/051696, dated Apr. 8 2016.
International Search Report for PCT/EP2016/051712, dated Mar. 23, 2016.
Todd, Charles, et al., "Volatile Silicone Fluids for Cosmetic Formulations," Cosmetics and Toiletries, vol. 91, Jan. 1976, pp. 29-32.

(Continued)

*Primary Examiner* — Abigail Vanhorn
*Assistant Examiner* — Mei Ping Chui
(74) *Attorney, Agent, or Firm* — The Marbury Law Group, PLLC

(57) ABSTRACT

The present invention relates to a process for treating the hair, which comprises: a) the application to the hair of a composition comprising one or more polymers containing a silicone unit bearing alkoxy-(aminomethyl)-silyl functional groups, b) the application to the hair of steam by means of a device that is capable of generating steam, step b) possibly preceding, following or being simultaneous with step a).

24 Claims, No Drawings

(56) References Cited

U.S. PATENT DOCUMENTS

| | | |
|---|---|---|
| 2014/0161756 A1 | 6/2014 | Beer et al. |
| 2014/0245542 A1 | 9/2014 | Schulze zur Wiesche et al. |
| 2014/0271750 A1* | 9/2014 | Schulze Zur Wiesche ............... A61Q 5/12 424/401 |
| 2015/0104397 A1 | 4/2015 | Small et al. |

FOREIGN PATENT DOCUMENTS

| | | | |
|---|---|---|---|
| EP | 0186507 A2 | 7/1986 | |
| EP | 0342834 A2 | 11/1989 | |
| EP | 0659393 A1 | 6/1995 | |
| EP | 0662314 A1 * | 7/1995 | .............. A45D 7/06 |
| EP | 0662314 A1 | 7/1995 | |
| FR | 1222944 A | 6/1960 | |
| FR | 1400366 A | 5/1965 | |
| FR | 1564110 A | 4/1969 | |
| FR | 1580545 A | 9/1969 | |
| FR | 2077143 A | 10/1971 | |
| FR | 2198719 A1 | 4/1974 | |
| FR | 2265781 A1 | 10/1975 | |
| FR | 2265782 A1 | 10/1975 | |
| FR | 2273492 A1 | 1/1976 | |
| FR | 2350384 A1 | 12/1977 | |
| FR | 2357241 A2 | 2/1978 | |
| FR | 2393573 A1 | 1/1979 | |
| FR | 2439798 A1 | 5/1980 | |
| FR | 2990131 A1 | 11/2013 | |
| FR | 3008888 A1 | 1/2015 | |
| GB | 839805 A | 6/1960 | |
| GB | 922457 A | 4/1963 | |
| GB | 1021400 A | 3/1966 | |
| GB | 1408388 A | 10/1975 | |
| GB | 1572626 A | 7/1980 | |
| JP | H08-24036 A | 1/1996 | |
| JP | H08-24037 A | 1/1996 | |
| JP | 2006-249002 A | 9/2006 | |
| JP | 2010-241812 A | 10/2010 | |
| JP | 2010-540137 A | 12/2010 | |
| JP | 2012-516313 A | 7/2012 | |
| JP | 2014-523447 A | 9/2014 | |
| JP | 2015-500280 A | 1/2015 | |
| LU | 75370 A1 | 2/1978 | |
| LU | 75371 A1 | 2/1978 | |
| WO | 2005/108495 A2 | 11/2005 | |
| WO | 2009/019165 A1 | 2/2009 | |
| WO | 2013/014140 A2 | 1/2013 | |
| WO | 2014/151667 A1 | 9/2014 | |
| WO | 2015/011258 A1 | 1/2015 | |
| WO | 2016/120321 A1 | 8/2016 | |
| WO | 2016/120322 A1 | 8/2016 | |

OTHER PUBLICATIONS

"Kosmeti sche Zusammensetzungen," IP.com Journal, IP.com, Inc., NY, XP013146799, Aug. 4, 2011.

"Table 31; Hair Fixative Polymers Commonly Used in Hair Spray Products ED—Dekker," Hair and Hair Care (Cosmetic Science and Technology)—Series Title: Cosmetic Science and Technology Series, vol. 17, XP007923230, Jan. 1, 1997, pp. 136-137.

Non-Final Office Action for copending U.S. Appl. No. 15/547,142, dated Nov. 19, 2018.

Notification of Reasons for Refusal for counterpart Japanese Application No. 2017-540121, dated Oct. 29, 2018.

Non-Final Office Action for co-pending U.S. Appl. No. 15/547,138, dated May 30, 2019.

Notice of Allowance for co-pending U.S. Appl. No. 15/547,142, dated Jul. 12, 2019.

* cited by examiner

PROCESS FOR TREATING THE HAIR WITH AT LEAST ONE SILICONE FUNCTIONALIZED WITH AT LEAST ONE ALKOXYSILANE UNIT, AND STEAM

CROSS REFERENCE TO RELATED APPLICATIONS

This is a national stage application of PCT/EP2016/051712, filed internationally on Jan. 27, 2016, which claims priority to French Application No. 1550706, filed on Jan. 29, 2015, both of which are incorporated by reference herein in their entireties.

The invention relates to a process for treating the hair using a composition comprising at least one particular silicone and steam.

Two major categories of hair shaping products are generally used: styling products and perming products.

Styling products allow non-permanent shaping of the hair. They are used on wet or dry hair before shaping by hand or using a brush or a comb. They are in the form of gels, foams, waxes, pastes, lacquers or sprays. After they have been applied to the hair and after drying, these products harden substantially. This is reflected by an unnatural, embodied, dry feel required for the hold and volume of the hairstyle. Moreover, they do not show good resistance to moisture, and a head of hair loses its shape when exposed to a humid atmosphere, all the more so in a hot and humid atmosphere. Thus, firstly, the general shape of the hairstyle is rapidly lost and, secondly, the hair becomes frizzy, more particularly in the case of hair that is naturally frizzy.

To improve the feel, it is known practice to use silicones, or silicone derivatives, in particular amino silicones and amino silicones bearing silanol functions that are capable of reacting together to form new bonds. Silicones give a natural, soft, non-greasy and non-set feel. They may also be partially water-resistant, which makes it possible to conserve the soft, natural feel. However, they cannot afford shaping of the head of hair or combat the appearance of frizziness, unless a very large amount of product is applied, which gives a greasy feel. As they only sparingly compensate for the dry feel when they are combined with other types of styling product such as fixing polymers, the combination of these two techniques remains relatively unsatisfactory.

Moreover, these styling products are removed on shampooing. They therefore need to be applied daily.

Perming products allow long-lasting shaping of a head of hair.

Generally, the technique used for permanently reshaping the hair consists, in a first stage, in opening the —S—S— disulfide bonds of keratin (cystine) by applying to the hair, which has been placed under tension beforehand (with curlers and other tensioning means), a reducing composition (reduction step) and then, preferably after having rinsed the head of hair thus treated, in reconstituting said disulfide bonds in a second stage by applying to the hair, which is still under tension, an oxidizing composition (oxidation step, also known as the fixing step) so as to finally give the hair the desired shape.

The new shape given to the hair by a chemical treatment such as that above is long-lasting and especially withstands the action of washing with water or with shampoos.

However, such a technique is not entirely satisfactory. Specifically, this technique is very effective for modifying the shape of the hair, but is very degrading to hair fibres.

These two systems do not afford sufficient cosmeticity and/or durability of the effect obtained.

Consequently, there is still a need for a hair treatment process for giving the hair the desired shape in a long-lasting manner, while at the same time having very good cosmetic properties.

The object of the present invention is, precisely, to satisfy at least one of these needs.

According to one of its aspects, the invention relates to a hair treatment process which comprises:

a) the application to the hair of a composition comprising one or more polymers containing a silicone unit bearing alkoxy-(aminomethyl)-silyl functional groups, b) the application to the hair of steam by means of a device that is capable of generating steam, step b) possibly preceding, following or being simultaneous with step a).

The process of the present invention makes it possible to obtain an improvement in the cosmetic properties, which persist for at least one wash.

Furthermore, when it is used with a hair-shaping device, for instance an iron, the process may in particular make it possible to obtain good shaping of the hair, such as straightening/relaxing, which is long-lasting and persistent with respect to shampooing. It may also make it possible to durably reduce the volume of the hair and the frizzy effect.

The process of the invention thus makes it possible to durably give the hair the desired shape, while at the same time having good cosmetic properties.

The process according to the invention comprises a step a) of applying a composition which comprises one or more polymers containing silicone unit bearing alkoxy-(aminomethyl)-silyl functional groups.

The polymer(s) containing a silicone unit bearing alkoxy-(aminomethyl)-silyl functional groups are preferably of formula (I) below:

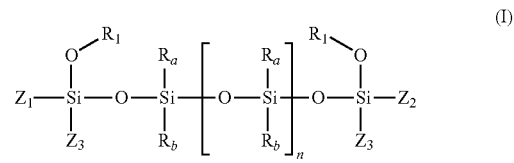

in which:
$Z_2$ represents a group —$CH_2$—$NR_3R_4$;
$Z_3$ represents a group $OR_5$ or $R_6$;
$R_1$ represents a $C_1$-$C_6$ alkyl group,
$R_3$ represents a hydrogen atom or a group $R_7$; $R_4$ represents a $C_1$-$C_6$ alkyl group or a $C_5$-$C_6$ cycloalkyl group; or
$R_3$ and $R_4$ possibly forming, with the nitrogen atom that bears them, a 5- to 8-membered heterocycle comprising from 1 to 3 heteroatoms,
$R_5$, $R_6$ and $R_7$, which may be identical or different, represent a $C_1$-$C_6$ alkyl group, and
$R_a$ and $R_b$, which may be identical or different, represent a $C_1$-$C_2$ alkyl group,
n represents an integer greater than 1.
Preferably, the $C_1$-$C_6$ alkyl groups are methyl or ethyl groups.
Preferably, $R_1$ is an ethyl group.
When $R_4$ represents a $C_5$-$C_6$ cycloalkyl group, it preferably represents a $C_6$ cycloalkyl group such as cyclohexyl.
Preferably, n ranges from 1 to 10 000, more preferably from 5 to 1000 and more preferentially from 8 to 400.

According to a particular embodiment of the invention, $Z_2$ represents a group —$CH_2$—$NR_3R_4$, $R_4$ represents an alkyl group, preferably a cyclohexyl, $R_3$ represents a hydrogen atom and $R_5$ represents an ethyl group.

According to a preferred embodiment of the invention, $R_3$ and $R_4$ form, with the nitrogen atom that bears them, a 5- to 8-membered heterocycle comprising from 1 to 3 heteroatoms. More preferably, $R_3$ and $R_4$ form, with the nitrogen that bears them, a cyclic group, preferably morpholino, and $R_5$ represents an ethyl group.

Preferably, $SiR_aR_b$—$[OSiR_aR_b]n$- of formula (I) is a unit derived from a linear silicone with a weight-average molecular weight of between 200 and 40 000 and more preferentially between 400 and 25 000 g/mol.

As examples of polymers corresponding to formula (I), mention will be made of:

polymers of formula (Ia)

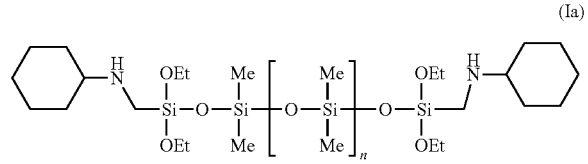
(Ia)

The polymers of formula (Ia) may be obtained by reacting a silicone bearing hydroxyl end groups with triethoxycyclohexylaminomethylsilane especially according to the techniques described in WO 2005/108 495.

According to a particular example, polymer (Iaa), corresponding to formula (Ia), is obtained according to the operating scheme presented above, starting with a silicone with a weight-average molecular mass Mw of 4750 g/mol.

polymers of formula (Ib)

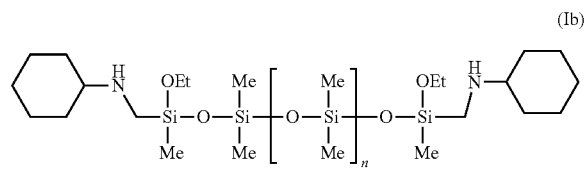
(Ib)

The polymers of formula (Ib) may be obtained by reacting a silicone bearing hydroxyl end groups with diethoxycyclohexylaminomethylmethylsilane especially according to the techniques described in WO 2005/108 495.

According to a particular example, polymer (Iba), corresponding to formula (Ib), is obtained according to the operating scheme presented above, starting with a silicone with a weight-average molecular mass Mw of 4750 g/mol.

polymers of formula (Ic)

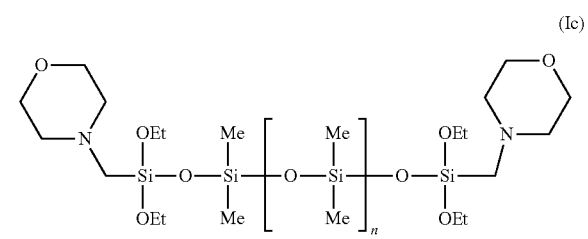
(Ic)

The polymers of formula (Ic) may be obtained by reacting a silicone bearing hydroxyl end groups with triethoxymorpholinomethylsilane especially according to the techniques described in WO 2009/019 165.

According to a particular example, polymer (Ica), corresponding to formula (Ic), is obtained according to the operating scheme presented above, starting with a silicone with a weight-average molecular mass Mw of 4750 g/mol.

According to another particular example, polymer (Icb), corresponding to formula (Ic), is obtained according to the operating scheme presented above, starting with a silicone with a weight-average molecular mass of 10 600 g/mol.

According to another particular example, polymer (Icc), corresponding to formula (Ic), is obtained according to the operating scheme presented above, starting with a silicone with a weight-average molecular mass of 14 600 g/mol.

According to another particular example, polymer (Icd), corresponding to formula (Ic), is obtained according to the operating scheme presented above, starting with a silicone with a weight-average molecular mass Mw of 21 100 g/mol.

According to another particular example, polymer (Ice), corresponding to formula (Ic), is obtained according to the operating scheme presented above, starting with a silicone with a weight-average molecular mass Mw of 550 g/mol.

According to another particular example, polymer (Icf), corresponding to formula (Ic), is obtained according to the operating scheme presented above, starting with a silicone with a weight-average molecular mass Mw of 1000 g/mol.

According to another particular example, polymer (Icg), corresponding to formula (Ic), is obtained according to the operating scheme presented above, starting with a silicone with a weight-average molecular mass Mw of 1200 g/mol.

According to another particular example, polymer (Ich), corresponding to formula (Ic), is obtained according to the operating scheme presented above, starting with a silicone with a weight-average molecular mass Mw of 1700 g/mol.

polymers of formula (Id)

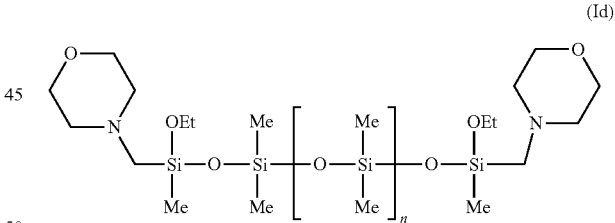
(Id)

The polymers of formula (Id) may be obtained by reacting a silicone bearing hydroxyl end groups with diethoxymorpholinomethylmethylsilane especially according to the techniques described in document WO 2009/019 165.

According to a particular example, the polymer of formula (Ida), corresponding to formula (Id), is obtained according to the operating scheme presented above, starting with a silicone with a weight-average molecular mass Mw of 4750 g/mol.

According to another particular example, the polymer of formula (Idb), corresponding to formula (Id), is obtained according to the operating scheme presented above, starting with a silicone with a weight-average molecular mass Mw of 10 600 g/mol.

According to another particular example, the polymer of formula (Idc), corresponding to formula (Id), is obtained according to the operating scheme presented above, starting with a silicone with a weight-average molecular mass Mw of 14 600 g/mol.

According to another particular example, the polymer of formula (Idd), corresponding to formula (Id), is obtained according to the operating scheme presented above, starting with a silicone with a weight-average molecular mass Mw of 21 100 g/mol.

The content of the polymer(s) containing a silicone unit bearing alkoxy-(aminomethyl)-silyl functional groups, preferably of formula (I), in the composition generally ranges from 0.1% to 100% by weight, preferably from 0.5% to 30% by weight and more particularly from 1% to 10% by weight relative to the total weight of the composition.

The process according to the invention may also use one or more catalysts for catalysing the hydrolysis-condensation reactions of the alkoxysilane functions of the polymer containing a silicone unit bearing alkoxy-(aminomethyl)-silyl functional groups.

The catalyst may be chosen from acids and bases.

The acid may be chosen from mineral acids and organic acids.

The acid may be chosen in particular from lactic acid, acetic acid, citric acid, tartaric acid, hydrochloric acid, sulfuric acid and phosphoric acid, preferably hydrochloric acid.

The base may be chosen from mineral bases and organic bases.

The base may be chosen from ammonia and sodium hydroxide.

The catalyst may also be chosen from alkoxysilane monomers, optionally bearing an amine function, such as aminopropyltriethoxysilane or octyltriethoxysilane.

The catalyst may be present in the composition used in the process according to the invention, or it may be mixed at the time of use with the composition, or alternatively may be applied sequentially to the hair before or after the composition, preferably before.

The catalyst(s) may represent from 0.0001% to 10% by weight, preferably from 0.001% to 5% by weight and more particularly from 0.01% to 2% by weight relative to the total weight of the composition containing them.

According to a preferred embodiment, the composition according to the invention may comprise one or more silicone compound(s), different from the polymer containing a silicone unit bearing alkoxy-(aminomethyl)-silyl functional groups, which may be solid or liquid, and volatile or non-volatile.

The silicone compound that may be used may be soluble or insoluble in the composition according to the invention; they may be in the form of oil, wax, resin or gum; silicone oils and gums are preferred.

Silicones are especially described in detail in Walter Noll's Chemistry and Technology of Silicones (1968), Academic Press.

The volatile silicones may be chosen from those with a boiling point of between 60° C. and 260° C. (at atmospheric pressure) and more particularly from:

i) cyclic polydialkylsiloxanes comprising from 3 to 7 and preferably 4 to 5 silicon atoms, such as
  octamethylcyclotetrasiloxane and decamethylcyclopentasiloxane.
  Mention may be made of the products sold under the name Volatile Silicone 7207 by Union Carbide or Silbione 70045 V 2 by Rhodia, Volatile Silicone 7158 by Union Carbide or Silbione 70045 V 5 by Rhodia.

cyclocopolymers of the dimethylsiloxane/methylalkylsiloxane type having the chemical structure:

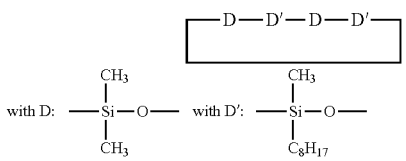

Mention may be made of Volatile Silicone FZ 3109 sold by the company Union Carbide.

mixtures of cyclic silicones with silicon-derived organic compounds, such as the mixture of octamethylcyclotetrasiloxane and of tetratrimethylsilylpentaerythritol (50/50) and the mixture of octamethylcyclotetrasiloxane and of 1,1'-oxy(2,2,2',2',3,3'-hexatrimethylsilyloxy)bisneopentane;

ii) linear polydialkylsiloxanes containing 2 to 9 silicon atoms, which generally have a viscosity of less than or equal to $5\times10^{-6}$ m2/s at 25° C., such as decamethyltetrasiloxane.

Other silicones belonging to this category are described in the article published in Cosmetics and Toiletries, Vol. 91, January 76, pp. 27-32—Todd & Byers Volatile silicone fluids for cosmetics; mention may be made of the product sold under the name SH 200 by the company Toray Silicone.

Among the non-volatile silicones, mention may be made, alone or as a mixture, of polydialkylsiloxanes and especially polydimethylsiloxanes (PDMS), polydiarylsiloxanes, polyalkylarylsiloxanes, silicone gums and resins, and also organopolysiloxanes (or organomodified polysiloxanes, or alternatively organomodified silicones) which are polysiloxanes comprising in their structure one or more organofunctional groups, generally attached via a hydrocarbon-based group, and preferably chosen from aryl groups, amine groups, alkoxy groups and polyoxyethylene or polyoxypropylene groups.

The organomodified silicones may be polydiarylsiloxanes, in particular polydiphenylsiloxanes, and polyalkylarylsiloxanes functionalized with the organofunctional groups mentioned previously. The polyalkylarylsiloxanes are particularly chosen from linear and/or branched polydimethyl/methylphenylsiloxanes and polydimethyl/diphenylsiloxanes.

Among the organomodified silicones, mention may be made of polyorganosiloxanes comprising:

polyethyleneoxy and/or polypropyleneoxy groups optionally comprising C6-C24 alkyl groups, such as dimethicone copolyols and especially those sold by the company Dow Corning under the name DC 1248 or the oils Silwet® L 722, L 7500, L 77 and L 711 by the company Union Carbide; or (C12)alkylmethicone copolyols and especially those sold by the company Dow Corning under the name Q2 5200;

substituted or unsubstituted amine groups, in particular C1-C4 aminoalkyl groups; mention may be made of the products sold under the names GP4 Silicone Fluid and GP7100 by the company Genesee, or under the names Q2-8220 and DC929 or DC939 by the company Dow Corning;

thiol groups, such as the products sold under the names GP 72 A and GP 71 from Genesee;

alkoxylated groups, such as the product sold under the name Silicone Copolymer F-755 by SWS Silicones and Abil Wax® 2428, 2434 and 2440 by the company Goldschmidt;

hydroxylated groups, for instance polyorganosiloxanes bearing a hydroxyalkyl function;

acyloxyalkyl groups, such as the polyorganosiloxanes described in U.S. Pat. No. 4,957,732;

anionic groups of the carboxylic acid type, as described, for example, in EP 186 507, or of the alkylcarboxylic type, such as the product X-22-3701 E from the company Shin-Etsu; or else of the 2-hydroxyalkylsulfonate or 2-hydroxyalkylthiosulfate type, such as the products sold by the company Goldschmidt under the names Abil® S201 and Abil® S255;

hydroxyacylamino groups, such as the polyorganosiloxanes described in patent application EP 342 834; mention may be made, for example, of the product Q2-8413 from the company Dow Corning.

The silicones may also be chosen from polydialkylsiloxanes, among which mention may be made mainly of polydimethylsiloxanes bearing trimethylsilyl end groups. Among these polydialkylsiloxanes, mention may be made of the following commercial products:

the Silbione® oils of the 47 and 70 047 series or the Mirasil® oils sold by Rhodia, such as, for example, the oil 70 047 V 500 000;

the oils of the Mirasil® series sold by the company Rhodia;

the oils of the 200 series from the company Dow Corning, such as DC200 with a viscosity of 60 000 mm$^2$/s;

the Viscasil® oils from General Electric and certain oils of the SF series (SF 96, SF 18) from General Electric.

Mention may also be made of polydimethylsiloxanes bearing dimethylsilanol end groups known under the name dimethiconol (CTFA), such as the oils of the 48 series from the company Rhodia.

In this category of polydialkylsiloxanes, mention may also be made of the products sold under the names Abil Wax® 9800 and 9801 by the company Goldschmidt, which are poly(C1-C20)dialkylsiloxanes.

Products that can be used more particularly in accordance with the invention are mixtures such as:

the mixtures formed from a polydimethylsiloxane hydroxylated at the chain end, or dimethiconol (CTFA), and from a cyclic polydimethylsiloxane, also known as cyclomethicone (CTFA), such as the product Q2 1401 sold by the company Dow Corning.

The polyalkylarylsiloxanes are particularly chosen from linear and/or branched polydimethyl/methylphenylsiloxanes and polydimethyl/diphenylsiloxanes with a viscosity ranging from $1\times10^{-5}$ to $5\times10^{-2}$ m$^2$/s at 25° C.

Among these polyalkylarylsiloxanes, examples that may be mentioned include the products sold under the following names:

the Silbione® oils of the 70 641 series from Rhodia;
the oils of the Rhodorsil® 70 633 and 763 series from Rhodia;
the oil Dow Corning 556 Cosmetic Grade Fluid from Dow Corning;
the silicones of the PK series from Bayer, such as the product PK20;
the silicones of the PN and PH series from Bayer, such as the products PN1000 and PH1000;
certain oils of the SF series from General Electric, such as SF 1023, SF 1154, SF 1250 and SF 1265.

Preferably, the silicone compound comprises at least one alkyl unit.

More preferably, the silicone compound is chosen from amodimethicone, bis-cetearyl amodimethicone, dimethiconol, dimethicone, vinyl dimethicone, caprylyl methicone, diphenylsiloxyphenyltrimethicone.

Even more preferably, the silicone compound is bis-cetearyl amodimethicone.

The cosmetic composition according to the invention may comprise the silicone compound in an amount ranging from 0.01% to 30% by weight, preferably from 0.1% to 10% by weight and better still from 0.2% to 5% by weight, relative to the total weight of the composition.

The composition may be aqueous or anhydrous. When it contains any, the composition preferably contains less than 5% by weight of water relative to the total weight of the composition.

The composition is preferably anhydrous. For the purposes of the present invention, the term "anhydrous composition" means a composition having a water content of less than 3% by weight, preferably less than 2% by weight relative to the total weight of the composition, and/or a composition which does not contain any added water, i.e. the water that may be present in the composition according to the invention is more particularly bound water, such as the water of crystallization of salts, or traces of water absorbed by the starting materials used in the production of the compositions.

The composition used in the process according to the invention may comprise one or more organic solvents.

The organic solvent(s) are preferably chosen from alcohols, alkanes, esters and silicones, and mixtures thereof.

The alcohols are linear or branched $C_1$-$C_6$ monoalcohols or polyols.

The esters may be natural or synthetic.

The esters may be chosen especially from plant oils and esters of fatty acids or of fatty alcohols, such as isopropyl myristate.

The alkanes may be chosen especially from linear or branched $C_6$-$C_{15}$ alkanes and liquid paraffins.

The silicones may be chosen especially from amino silicones, silicones bearing alkyl end groups, cyclic silicones comprising from 4 to 6 silicon atoms and linear polydimethylsiloxanes.

Preferably, the organic solvent is chosen from ethanol, propanol, isopropanol, glycerol, undecane, tridecane, isododecane, isopropyl myristate, ethyl adipate, ethyl acetate, linear low-molecular-weight silicones or cyclic silicones such as cyclopentasiloxane, amino silicones and silicones bearing alkyl end groups, and also mixtures thereof.

According to a preferred embodiment, the solvent is chosen from linear low-molecular-weight silicones, cyclic silicones, isododecane, undecane, tridecane and isopropanol.

The organic solvents used in the composition used in the process of the invention are preferably liquids which preferably have a viscosity at 25° C. and at atmospheric pressure of less than or equal to 100 cSt.

The organic solvent(s) may represent from 1% to 99.9%, preferably from 70% to 99.5% by weight and better still from 70% to 99% by weight relative to the total weight of the composition.

The composition may also contain one or more additives chosen from conditioning agents, nonionic, anionic and amphoteric surfactants, vitamins and provitamins including panthenol, water-soluble and liposoluble sunscreens, fillers and solid particles, for instance mineral and organic, coloured or uncoloured pigments, nacreous agents and opacifiers, glitter flakes, mineral fillers, dyes, sequestrants, plasticizers, solubilizers, acidifying agents, basifying agents, mineral and organic thickeners, antioxidants, antifoams, moisturizers, emollients, hydroxy acids, penetrants, fragrances and preserving agents.

Needless to say, a person skilled in the art will take care to select the optional additional compounds and/or the amount thereof such that the advantageous properties of the compositions used according to the invention are not, or are not substantially, adversely affected by the envisioned addition.

The composition may be in the form of a solution, a dispersion or an emulsion. The polymer may be emulsified as an oil-in-water or water-in-oil emulsion or as a multiple emulsion.

The composition may be in the form of a foam, a gel, a serum, a cream, a paste, a wax, a liquid lotion or a lacquer. Preferably, the composition is in the form of a serum or a liquid lotion.

The composition may be packaged in a pump-dispenser bottle or in an aerosol device. As a variant, it may be envisaged to condition it in a container intended to be received in a rechargeable application device.

As indicated previously, the composition may or may not contain a catalyst.

According to a particular embodiment, the application may be performed in a single stage. In this case, a composition including one or more polymers containing a silicone unit bearing alkoxy-(aminomethyl)-silyl functional groups, preferably of formula (I), and optionally one or more catalysts as defined previously, will be applied.

In this one-stage embodiment, the composition applied to the hair may result from the mixing of a composition comprising one or more polymers containing a silicone unit bearing alkoxy-(aminomethyl)-silyl functional groups, preferably of formula (I), and of a composition comprising one or more catalysts as defined previously.

According to another embodiment, the application may be performed in two stages: in a step (A) the composition comprising one or more catalysts as defined previously is applied, in a step (B) the composition comprising one or more polymers containing a silicone unit bearing alkoxy-(aminomethyl)-silyl functional groups, preferably of formula (I), is applied. In this embodiment, step (A) may be performed, followed by step (B), or alternatively step (B) may be performed, followed by step (A), with or without intermediate drying. Preferably, step (A) is performed, followed by step (B). In this particular embodiment, intermediate drying is preferably performed.

According to another preferred embodiment, the process according to the invention comprises a step of applying to the hair a pre-treatment composition comprising one or more organosilanes before the application to the hair of the composition comprising one or more polymers containing a silicone unit bearing alkoxy-(aminomethyl)-silyl functional groups.

Preferably, the organosilanes are chosen from the compounds of formula (I) and/or oligomers thereof:

in which:

R1' is a cyclic or acyclic, linear or branched, saturated or unsaturated C1-C22, in particular C2-C20, hydrocarbon-based chain, which may be substituted with a group chosen from amine groups NH2 or NHR (R being a linear or branched C1-C20, in particular C1-C6, alkyl, a C3-C40 cycloalkyl or a C6-C30 aromatic radical); the hydroxyl group (OH), a thiol group, an aryl group (more particularly benzyl), which is possibly substituted with an NH2 or NHR group; it being possible for R'1 to be interrupted with a heteroatom (O, S or NH) or a carbonyl group (CO), R'2 and R'3, which may be identical or different, represent a linear or branched alkyl group comprising from 1 to 6 carbon atoms, y denotes an integer ranging from 0 to 3, z denotes an integer ranging from 0 to 3, and x denotes an integer ranging from 0 to 2, with x+y+z=3.

The term "oligomer" is intended to mean the polymerization products of the compounds of formula (I) comprising from 2 to 10 silicon atoms.

Preferably, R'1 is a linear or branched, preferably linear, saturated C1-C22, in particular C2-C12, hydrocarbon-based chain, which may be substituted with an amine group NH2 or NHR (R═C1-C20, in particular C1-C6, alkyl).

Preferably, R'2 represents an alkyl group comprising from 1 to 4 carbon atoms, better still a linear alkyl group comprising from 1 to 4 carbon atoms, and preferably the ethyl group.

Preferably, z ranges from 1 to 3.

Preferably, y=0.

Preferentially, z=3, and therefore x=y=0.

In one embodiment of the invention, R'1 represents a linear alkyl group comprising from 7 to 18 carbon atoms and more particularly from 7 to 12 carbon atoms, or a C1-C6, preferably C2-C4, aminoalkyl group. More particularly, R'1 represents an octyl group.

In one embodiment of the invention, R'1 is a linear or branched, saturated or unsaturated C1-C22 hydrocarbon-based chain, substituted with an amine group NH2 or NHR (R═C1-C20, in particular C1-C6, alkyl, C3-C40 cycloalkyl or C6-C30 aromatic). In this variant, R'1 preferably represents a C1-C6, preferably C2-C4, amino-alkyl group.

Preferably, the composition according to the invention comprises one or more organosilanes chosen from octyltriethoxysilane (OTES), dodecyltriethoxysilane, octadecyltriethoxysilane, hexadecyltriethoxysilane, 3-aminopropyltriethoxysilane (APTES), 2-aminoethyltriethoxysilane (AETES), 3-aminopropylmethyldiethoxysilane, N-(2-aminoethyl)-3-aminopropyltriethoxysilane, 3-(m-aminophenoxy)propyltrimethoxysilane, p-aminophenyltrimethoxysilane, N-(2-aminoethylaminomethyl) phenethyltrimethoxysilane, and oligomers thereof; and more particularly chosen from octyltriethoxysilane (OTES) and 3-aminopropyltriethoxysilane (APTES), and oligomers thereof.

The organosilanes used in the composition of the invention, in particular those comprising a basic function, may be partially or totally neutralised in order to improve the water-solubility thereof. In particular, the neutralising agent may be chosen from organic or inorganic acids, such as citric acid, tartaric acid, lactic acid or hydrochloric acid.

Preferably, the optionally neutralised organosilanes according to the invention are water-soluble and in particular soluble at a concentration of 2%, better still at a concentration of 5% and even better still at a concentration of 10% by weight in water at a temperature of 25° C. and at atmospheric pressure (1 atm). The term "soluble" is intended to mean the formation of a single macroscopic phase.

The pre-treatment composition may be aqueous or anhydrous, preferably aqueous.

Preferably, the pre-treatment composition comprises the organosilane(s) in an amount ranging from 0.1% to 25% by weight, preferably from 0.2% to 10% by weight and even better still from 0.3% to 8% by weight, relative to the total weight of the composition.

The pre-treatment composition comprising the organosilanes can be applied on dry or wet hair, preferably on wet hair.

The process according to the invention may be performed using one or more compositions packaged in a device containing several compartments, comprising:
a first compartment containing a composition comprising one or more polymers containing a silicone unit bearing alkoxy-(aminomethyl)-silyl functional groups, preferably of formula (I);
a second compartment containing a composition comprising one or more catalysts as defined previously.

The device according to the invention may be intended for a one-stage or a two-stage application.

In the case of a one-stage application, the compositions of the first and second compartments may be dispensed simultaneously at the time of application.

In the process according to the invention, the composition that has just been described is applied to wet or dry hair.

According to the invention, the process also comprises a step b) of applying steam to the hair by means of a device that is capable of generating steam.

The application of steam may be repeated several times on the same fibres; however, it is possible to obtain a very good cosmetic result after a single application of steam.

The application of steam may be performed using any device known per se for generating the amount of steam of use in the process of the invention. According to a particular embodiment, this device is portable, i.e. the tank for generating steam is in contact with the part of the device comprising the steam-dispensing orifices.

The steam may be dry. The term "dry steam" means a gas which contains only water molecules in gaseous form.

The steam may alternatively be wet. The term "wet steam" means a gas which contains water molecules in gaseous form and water molecules in liquid form.

This steam application step may precede, follow or be simultaneous with the step of applying the composition that has just been described.

Preferably, the process according to the invention comprises a step of applying steam after step a).

According to a particular embodiment, the process according to the invention comprises two steam application steps, preferably after step a).

The amount of steam may be, limits inclusive, between 0.5 and 60 g/min, preferably between 1 and 20 g/min, more preferably 2 and 10 g/min and better still 2 and 5 g/min.

Preferably, the application time of steam on the hair, per lock, ranges from 1 second to 50 minutes, preferably from 1 second to 10 minutes and more preferably from 1 second to 1 minute. For example, the application time of steam on the hair may be from about 10 to 15 seconds.

According to a particular embodiment, the steam applied to the hair contains one or more cosmetic active agents and/or ingredients such as a fragrance, a shaping or conditioning active agent, etc.

The process according to the invention may also comprise a step of heating the hair at a temperature between, limits inclusive, 50° C. and 250° C., preferably 90° C. and 250° C., more preferably 120° C. and 230° C., and even better still between 150° C. and 230° C.

The heating step may precede, follow or be simultaneous with the steam application step b).

Preferably, the heating step may follow the steam application step b).

According to a particular embodiment, the process of the invention comprises a first step of applying steam followed by a step of heating and of simultaneous application of steam.

The step of heating the hair may be performed with any type of device known in the art for obtaining a temperature on the hair of at least 50° C.

The heating step may especially be performed using a heating device chosen from a straightening iron, a curling iron, a crimping iron, a waving iron, a hair drying hood or a hairdryer, preferably using a straightening iron.

According to a particular embodiment, the application of steam and the heating of the hair are performed by a single device, preferably a device chosen from a steam-generating straightening iron, a steam-generating curling iron, a steam-generating crimping iron and a steam-generating waving iron, more preferably by a steam-generating straightening iron.

According to a preferred embodiment, the application of steam and the heating of the hair are performed by a single device in which the application of steam and the heating are dissociated.

In other words, for a treated lock of hair, the steam application step and the heating step are not performed simultaneously on the same portion of hair, it nevertheless being possible for these two steps to be performed with the same device configured to form these two steps successively. In particular, the orifices through which the steam is dispensed are outside the hot plate of the iron. Alternatively, two separate device can be used to carry out these unconnected stages.

The invention is illustrated in greater detail in the examples that follow, which are given as non-limiting illustrations of the invention.

EXAMPLES

The following compositions were prepared for performing the process of the invention, the contents being expressed on a weight basis relative to the total weight of the composition:

|  | A | B | C | D | E |
|---|---|---|---|---|---|
| Polymer Ic (MW = 5200) | 2.5 | 20.0 | 10.0 | — | 2.5 |
| Iron oxides (and) mica (51.6/48.4) | — | 5.0 | 5.0 | 5.0 | — |
| Isopropyl alcohol | qs 100 | qs 100 | qs 100 | qs 100 | — |
| Cyclopentasiloxane |  |  |  |  | qs 100 |

Example 1

Composition A was applied to locks of natural frizzy dry hair, with a bath ratio of 0.15 g/g.

According to a first process (P1) according to the invention, after applying composition A, each lock was treated twice with straightening tongs heated to 210° C. applying dry steam with a flow rate of 3.3 g/min.

According to a second process (P2) according to the invention, after applying composition A, dry steam was applied to the locks using a steam-generating device with a flow rate of 3.3 g/min, each lock being treated with the device five times. Next, each lock was treated twice with straightening tongs heated to 210° C. applying dry steam with a flow rate of 3.3 g/min.

According to a third process (P3), after applying composition A, each lock was treated twice with straightening tongs heated to 210° C.

The amount of silicon on the hair treated via the various processes at t0, i.e. just after the steps of the processes, and after 1 shampoo wash, was measured by X-ray fluorescence spectrometry.

The results are given in the table below, in which the amount of silicon is indicated in µg per g of hair.

|  | P1 (invention) | P2 (invention) | P3 |
|---|---|---|---|
| at t0 | 1628 | 1682 | 1967 |
| after 1 shampoo wash | 1101 | 1462 | 894 |

It is found that the amount of silicon originating from polymer Ic after one shampoo wash is greater on the hair that has undergone a steam treatment (P1 and P2 relative to P3), this amount increasing further when an additional steam treatment was performed (P2 relative to P1).

Example 2

Composition B was applied to locks of natural dry grey hair containing 90% white hairs, with a bath ratio of 0.3 g/g.

According to a process P4, after applying composition B, each lock was treated with straightening tongs heated to 210° C.

According to a process P5 according to the invention, after applying composition B, dry steam was applied to the locks using a steam-generating device with a flow rate of 3.3 g/min, each lock being treated once with the device, each treatment lasting 10 seconds. Each lock was then treated with straightening tongs heated to 210° C.

According to a process P6 according to the invention, after applying composition B, dry steam was applied to the locks using a steam-generating device with a flow rate of 3.3 g/min, each lock being treated with the device five times, each treatment lasting 10 seconds. Each lock was then treated with straightening tongs heated to 210° C.

The persistence of red nacre deposited during the process was evaluated visually at t0 and after 2 shampoo washes. The following results were obtained:

|  | P4 | P5 (invention) | P6 (invention) |
|---|---|---|---|
| at t0 | +++ | +++ | +++ |
| after 2 shampoo washes | − | + | ++ |

+++: very strong red intensity
++: strong red intensity
+: moderate red intensity
−: weak red intensity
−−: very weak to zero red intensity It is found that the persistence of the composition on the hair is increased with the steam treatment, the persistence increasing with the amount of steam applied.

Example 3

The following processes were performed on locks of natural dry grey hair containing 90% white hairs, the compositions having been applied to the hair with a bath ratio of 0.3 g/g.

According to a process P7, composition D was applied to the locks and left to dry at room temperature.

According to a process P8, composition C was applied to the locks and left to dry at room temperature.

According to a process P9, composition D was applied to the locks. Each lock was then treated twice with straightening tongs heated to 210° C.

According to a process P10, composition C was applied to the locks. Each lock was then treated twice with straightening tongs heated to 210° C.

According to a process P11, composition D was applied to the locks. Each lock was then treated twice with straightening tongs heated to 210° C. applying dry steam with a flow rate of 3.3 g/min. Each treatment lasted 15 seconds.

According to a process P12 according to the invention, composition C was applied to the locks. Each lock was then treated twice with straightening tongs heated to 210° C. applying dry steam with a flow rate of 3.3 g/min. Each treatment lasted 15 seconds.

The persistence of red nacre deposited during the process was evaluated visually at t0, after one shampoo wash and after two shampoo washes.

|  | P7 | P8 | P9 | P10 | P11 | P12 (invention) |
|---|---|---|---|---|---|---|
| At t0 | +++ | +++ | +++ | +++ | +++ | +++ |
| After 1 shampoo wash | −− | − | −− | ++ | −− | ++ |
| after 2 shampoo washes | −− | −− | −− | + | −− | ++ |

+++: very strong red intensity
++: strong red intensity
+: moderate red intensity
−: weak red intensity
−−: very weak to zero red intensity It is found that the persistence of the composition on the hair is increased with the steam treatment, the persistence increasing with the amount of steam applied. In particular, it is found that a steam treatment combined with heat increases the persistence of the composition when compared with a heat treatment alone.

4) Example 4

A lock of natural frizzy hair that has undergone no treatment (width control) and such a lock that has undergone various treatments described below were placed in a humid chamber, at 80% relative humidity, for 24 hours. The width of these locks was then measured to evaluate the volume uptake in a humid atmosphere.

In particular these measurements were taken on locks for which processes P13 to P15 below were performed.

According to a process P13, each lock was treated twice with straightening tongs heated to 210° C.

According to a process P14, composition E was applied to locks of dry hair, with a bath ratio of 0.15 g/g. Each lock was then treated twice with straightening tongs heated to 210° C.

According to a process P15 according to the invention, composition E was applied to locks of dry hair, with a bath ratio of 0.15 g/g. Dry steam was then applied to the locks using a steam-generating device with a flow rate of 3.3 g/min, each lock being treated once with the device, each treatment lasting 15 seconds. Each lock was then treated twice with straightening tongs heated to 210° C.

The following results were obtained.

|  | Width control | P13 2* Heat | P14 Polymer + 2*heat | P15 Polymer + 1*steam + 2*heat |
|---|---|---|---|---|
| Width (cm) | 9.5 | 9.0 | 6.0 | 5.0 |

It is found that the use of a treatment with the polymer combined with a steam treatment and a heat treatment makes it possible to increase the humidity resistance of the straightening when compared with a heat treatment alone and also when compared with a treatment with the polymer combined with a heat treatment.

The process according to the invention thus makes it possible to durably reduce the volume of the hair in a humid environment.

Example 5

The following compositions were prepared for performing the process of the invention, the contents being expressed on a weight basis relative to the total weight of the composition:

|  | F | G |
|---|---|---|
| Polymer Ic (MW = 11100) | 5.0 | 5.0 |
| Bis-cetearyl amodimethicone | — | 2.0 |
| Cyclopentasiloxane | qs 100 | qs 100 |

The following processes were performed on locks of natural frizzy wet hair.

According to one process P16, the lock was treated twice with straightening tongs heated to 210° C. applying dry steam with a flow rate of 3.3 g/min. Each treatment lasted 15 seconds.

According to one process P17, composition F was applied to the lock, with a bath ratio of 0.15 g/g. Then, the lock was treated twice with straightening tongs heated to 210° C. applying dry steam with a flow rate of 3.3 g/min. Each treatment lasted 15 seconds.

According to one process P18, composition G was applied to the lock, with a bath ratio of 0.15 g/g. Then, the lock was treated twice with straightening tongs heated to 210° C. applying dry steam with a flow rate of 3.3 g/min. Each treatment lasted 15 seconds.

Then, the locks described above were placed in a humid chamber, at 80% relative humidity, for 24 hours.

The volume uptake in a humid atmosphere and the feel of the lock have been evaluated.

At $T_{24H}$, the volume of the lock treated according to process P17 was significantly reduced compared to the volume of the lock treated according to process P16. The volume of lock treated according to process P18 was significantly reduced compared to the volume of the lock treated according to process P17.

It is found that the use of a treatment with the polymer and a silicone compound makes it possible to increase again the humidity resistance of the straightening when compared with treatment with the polymer alone.

In addition, the feel of the lock treated according to process P17 is softer and smoother than the feel of the lock treated according to process P16. The feel of the lock treated according to process P18 is softer and smoother than the feel of the lock treated according to process P17.

It is found that the use of a treatment with the polymer and a silicone compound makes it possible to improve again the feel of the lock when compared with treatment with the polymer alone.

Example 6

The following pre-treatment composition was prepared, the contents being expressed on a weight basis relative to the total weight of the composition:

|  | H |
|---|---|
| Aminopropyltriethoxysilane | 5.0 |
| Lactic acid | Qs pH |
| Water | Qs 100 |

The following processes were performed on locks of natural frizzy dry hair.

According to one process P19, the lock was treated twice with straightening tongs heated to 210° C. applying dry steam with a flow rate of 3.3 g/min. Each treatment lasted 15 seconds. Then, the lock was washed with a shampoo.

According to one process P20, composition F was applied to the lock, with a bath ratio of 0.15 g/g. Then, the lock was treated twice with straightening tongs heated to 210° C. applying dry steam with a flow rate of 3.3 g/min. Each treatment lasted 15 seconds. Then, the lock was washed with a shampoo.

According to one process P21, composition H was applied to the lock, with a bath ratio of 0.15 g/g. Then, composition F was applied to the lock, with a bath ratio of 0.15 g/g. And then, the lock was treated twice with straightening tongs heated to 210° C. applying dry steam with a flow rate of 3.3 g/min. Each treatment lasted 15 seconds. Then, the lock was washed with a shampoo.

The volume of the hair after one shampoo was then evaluated.

The volume of the lock treated according to process P20 was significantly reduced compared to the volume of the lock treated according to process P19. The volume of lock treated according to process P21 was significantly reduced compared to the volume of the lock treated according to process P20.

It is found that the use of a pre-treatment with an organosilane improve again the resistance of the straightening after one shampoo (volume decrease, less frizziness).

According to one process P22, composition H was applied to the lock, with a bath ratio of 0.15 g/g. Then, composition G was applied to the lock, with a bath ratio of 0.15 g/g. And then, the lock was treated twice with straightening tongs heated to 210° C. applying dry steam with a flow rate of 3.3 g/min. Each treatment lasted 15 seconds. Then, the lock was washed with a shampoo.

Then, in each process P19 to P22, each lock was washed with a shampoo and treated twice with straightening tongs heated to 210° C. applying dry steam with a flow rate of 3.3 g/min, each treatment lasted 15 seconds, until 10 times (10 shampoos followed by 10 straightening).

After 10 shampoos, the volume of the lock treated according to process P20 was reduced compared to the volume of the lock treated according to process P19. The volume of lock treated according to process P22 was significantly reduced compared to the volume of the lock treated according to process P20.

It is found that the use of a pre-treatment with an organosilane improve the persistence of the resistance of the straightening after shampoos (volume decrease, less frizziness).

Furthermore, the disentangling of wet hair treated with process P22 is also improved after ten shampoos compared to wet hair treated with process P19.

After each shampoo and straightening treatment, the locks described above were placed in a humid chamber, at 80% relative humidity, for 24 hours. (P19', P20' and P22') Then the volume uptake in a humid atmosphere was evaluated.

The volume of the lock treated according to process P'20 was significantly reduced compared to the volume of the lock treated according to process P19'. The volume of lock treated according to process P22' was significantly reduced compared to the volume of the lock treated according to process P20'.

It is found that the use of the polymer makes it possible to increase the persistence of the humidity resistance of the straightening.

It is also found that the use of a pre-treatment with an organosilane improves again the persistence of the humidity resistance of the straightening.

The invention claimed is:

1. A method for treating hair, comprising:
(a) applying a composition comprising at least one polymer containing a silicone unit bearing alkoxy-(aminomethyl)-silyl functional groups chosen from compounds according to formula (I) below:

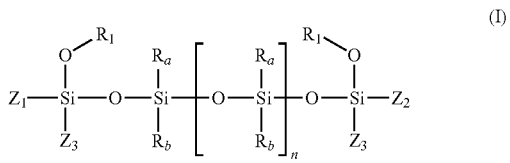

(I)

wherein:
$Z_2$ is chosen from —$CH_2$—$NR_3R_4$ groups;
$Z_3$ is chosen from $OR_5$ groups or a $R_6$ group;
$R_1$ is chosen from $C_1$-$C_6$ alkyl groups;
$R_3$ is chosen from a hydrogen atom or a $R_7$ group and $R_4$ is chosen from $C_1$-$C_6$ alkyl groups or $C_5$-$C_6$ cycloalkyl groups, or $R_3$ and $R_4$ may form, with the nitrogen atom that bears them, a 5- to 8-membered heterocycle comprising from 1 to 3 heteroatoms;
$R_5$, $R_6$, and $R_7$, which may be identical or different, are chosen from $C_1$-$C_6$ alkyl groups;
$R_a$ and $R_b$, which may be identical or different, are chosen from $C_1$-$C_2$ alkyl groups; and
n is an integer ranging from 1 to 10,000, and
(b) applying steam to the hair by a device capable of generating steam;
wherein the steam is applied to the hair prior to, subsequent to, or simultaneously with applying the composition.

2. The method according to claim 1, wherein the steam is applied to the hair subsequent to applying the composition.

3. The method according to claim 1, wherein the steam output ranges from about 0.5 g/min to about 60 g/min.

4. The method according to claim 1, further comprising heating the hair to a temperature ranging from about 50° C. to about 250° C., wherein the heat is applied to the hair prior to, subsequent to, or simultaneously with applying the steam.

5. The method according to claim 4, wherein the heating is performed using a heating device chosen from a straightening iron, a curling iron, a crimping iron, a waving iron, a hair drying hood, or a hairdryer.

6. The method according to claim 5, wherein applying steam and the heating of the hair are performed by a single device chosen from a steam-generating straightening iron, a steam-generating curling iron, a steam-generating crimping iron, or a steam-generating waving iron.

7. The method according to claim 6, wherein applying steam and the heating of the hair are performed by a single device, wherein the application of steam and the heating are dissociated.

8. The method according to claim 1, wherein the $C_1$-$C_6$ alkyl groups are chosen from methyl or ethyl groups.

9. The method according to claim 1, wherein $R_3$ and $R_4$ form, with the nitrogen atom that bears them, a 5- to 8-membered heterocycle comprising from 1 to 3 heteroatoms.

10. The method according to claim 1, wherein $R_3$ and $R_4$ form, with the nitrogen that bears them, a morpholino group, and $R_5$ is an ethyl group.

11. The method according to claim 1, wherein $SiR_aR_b$—[$OSiR_aR_b$]n- of formula (I) is a unit derived from a linear silicone, wherein the $SiR_aR_b$—[$OSiR_aR_b$]n- of formula (I) has a weight-average molecular mass (Mw) ranging from about 200 g/mol to about 40,000 g/mol.

12. The method according to claim 1, wherein the at least one polymer containing a silicone unit bearing alkoxy-(aminomethyl)-silyl functional groups is present in an amount ranging from 0.1% to 100% by weight, relative to the total weight of the composition.

13. The method according to claim 1, wherein the composition further comprises at least one organic solvent chosen from alcohols, alkanes, esters, silicones, or mixtures thereof.

14. The method according to claim 13, wherein the at least one organic solvent is present in an amount ranging from 1% to 99.9% by weight, relative to the total weight of the composition.

15. The method according to claim 1, wherein the composition further comprises water in an amount less than 5% by weight, relative to the total weight of the composition.

16. The method according to claim 1, wherein the composition further comprises at least one silicone compound different from the at least one polymer containing a silicone unit bearing alkoxy-(aminomethyl)-silyl functional groups.

17. The method according to claim 1, wherein the composition further comprises at least one silicone compound comprising at least one alkyl unit.

18. The method according to claim 1, further comprising applying to the hair a pre-treatment composition, the pre-treatment composition comprising at least one organosilane, wherein the pre-treatment composition is applied to the hair prior to the composition comprising at least one polymer containing a silicone unit bearing alkoxy-(aminomethyl)-silylfunctional groups.

19. The method according to claim 18, wherein the at least one organosilane is chosen from compounds according to formula (II) below, oligomers thereof, or mixtures thereof:

(II)

wherein:
R'1 is chosen from a cyclic or acyclic, linear or branched, saturated or unsaturated C1-C22 hydrocarbon-based chain, wherein the chain is optionally substituted with a group chosen from amine groups NH2 or NHR, wherein R is chosen from a linear or branched C1-C20 alkyl, a C3-C40 cycloalkyl, or a C6-C30 aromatic radical; a hydroxyl group (OH), a thiol group, an aryl group optionally substituted with an NH2 or NHR group; it being possible for R'1 to be interrupted with a heteroatom or a carbonyl group, R'2 and R'3, which may be identical or different, are chosen from a linear or branched alkyl group comprising from 1 to 6 carbon atoms, y is an integer ranging from 0 to 3, z is an integer ranging from 0 to 3, and x is an integer ranging from 0 to 2, wherein x+y+z=3.

20. The method according to claim 19, wherein the at least one organosilane of formula (II) is chosen from octyltriethoxysilane (OTES), dodecyltriethoxysilane, octadecyltriethoxysilane, hexadecyltriethoxysilane, 3-aminopropyltriethoxysilane (APTES), 2-aminoethyltriethoxysilane (AETES), 3-aminopropylmethyldiethoxysilane, N-(2-aminoethyl)-3-aminopropyltriethoxysilane, 3-(m-aminophenoxy)propyltrimethoxysilane, p-aminophenyltrimethoxysilane, or N-(2-aminoethylaminomethyl)phenethyltrimethoxysilane.

21. The method according to claim 1, wherein the composition further comprises at least one catalyst.

22. The method according to claim 21, wherein the at least one catalyst is chosen from organic or mineral basic compounds, organic or mineral acids, or mixtures thereof.

23. The method according to claim 21, wherein the at least one catalyst is present in an amount ranging from about 0.0001% to about 10% by weight, relative to the total weight of the composition.

24. The method according to claim 1, wherein the method further comprises applying at least one catalyst to the hair before or after the composition comprising the at least one polymer containing a silicone unit bearing alkoxy-(aminomethyl)-silyl functional groups.

* * * * *